(12) United States Patent
Wassie et al.

(10) Patent No.: US 12,139,448 B2
(45) Date of Patent: Nov. 12, 2024

(54) UREA AND MELAMINE PRODUCTION

(71) Applicant: Stamicarbon B.V., Sittard (NL)

(72) Inventors: Solomon Assefa Wassie, Eindhoven (NL); Rahul Patil, Maastricht (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 18/293,947

(22) PCT Filed: Oct. 13, 2023

(86) PCT No.: PCT/NL2023/050536
§ 371 (c)(1),
(2) Date: Jan. 31, 2024

(87) PCT Pub. No.: WO2024/080874
PCT Pub. Date: Apr. 18, 2024

(65) Prior Publication Data
US 2024/0262788 A1    Aug. 8, 2024

(30) Foreign Application Priority Data
Oct. 14, 2022 (EP) .................... 22201711

(51) Int. Cl.
*C07D 251/60* (2006.01)
*B01J 19/00* (2006.01)
*C07C 273/04* (2006.01)
*C07C 273/12* (2006.01)

(52) U.S. Cl.
CPC ......... *C07C 273/12* (2013.01); *B01J 19/0046* (2013.01); *C07C 273/04* (2013.01); *C07D 251/60* (2013.01); *B01J 2219/00452* (2013.01); *B01J 2219/00477* (2013.01); *B01J 2219/00495* (2013.01)

(58) Field of Classification Search
CPC .................................................. C07D 251/60
See application file for complete search history.

(56) References Cited

U.S. PATENT DOCUMENTS

| | | |
|---|---|---|
| 2004/0162429 A1 | 8/2004 | Noe et al. |
| 2006/0052637 A1 | 3/2006 | Porro |
| 2007/0282102 A1 | 12/2007 | Brunengo et al. |
| 2011/0275806 A1 | 11/2011 | Borrini et al. |
| 2015/0119603 A1 | 4/2015 | Van Den et al. |
| 2016/0194293 A1 | 7/2016 | Zardi et al. |
| 2016/0318883 A1 | 11/2016 | Mennen |
| 2019/0015811 A1 | 1/2019 | Coloma et al. |
| 2020/0385339 A1 | 12/2020 | Patil et al. |
| 2023/0265051 A1 | 8/2023 | Geurts |

FOREIGN PATENT DOCUMENTS

| | | |
|---|---|---|
| DE | 2053358 A1 | 5/1972 |
| EP | 2385043 A1 | 11/2011 |
| WO | 2022177438 A1 | 8/2022 |

OTHER PUBLICATIONS

Ullmann's Encyclopaedia of Industrial Chemistry, Chapter Urea, 2010.
"Urea-melamine plant integration", Nitrogen + Syngas 321, Jan.-Feb. 2013, p. 44-54.
Ullmann's Encyclopaedia of Industrial Chemistry, Chapter Melamine, 2003.
International Search Report and Written Opinion in PCT Application No. PCT/NL2023/050536, mailed Jan. 24, 2024 (10 pages).

*Primary Examiner* — John S Kenyon
(74) *Attorney, Agent, or Firm* — Leason Ellis LLP (57) ABSTRACT

The disclosure pertains to urea production with, in series, an MP carbamate condenser for condensing at least urea synthesis section off-gas, gas/liquid separation giving a gas stream and a liquid stream, and a second carbamate condenser receiving off-gas from melamine production and said liquid stream.

19 Claims, 1 Drawing Sheet

UREA AND MELAMINE PRODUCTION

CROSS-REFERENCE TO RELATED PATENT APPLICATIONS

This application is a U.S. National Stage Application under 35 U.S.C. § 371 of International Patent Application No. PCT/NL2023/050536, filed Oct. 13, 2023, which claims the benefit of priority of European Patent Application No. 22201711.3, filed Oct. 14, 2022, both of which are incorporated by reference in their entireties.

FIELD

The invention pertains to an integrated process for the production of urea and melamine.

INTRODUCTION

Melamine plants yield an off-gas comprising substantial amounts of $CO_2$ and $NH_3$. It is desired to supply these gases to a urea plant where these gases are used as reactants. Various possibilities for coupling and integrating urea plants and melamine plants have been proposed in the art.

Example urea production plants are illustrated in Ullmann's Encyclopaedia of Industrial Chemistry, Chapter Urea, 2010; hereinafter Ullmann's Urea, 2010. Some well-known types of urea plants include conventional plants (with no high pressure stripping), and stripping plants using e.g. the Stamicarbon $CO_2$ stripping design, the Toyo design with $CO_2$ stripping, and the Snamprogetti design with thermal stripping.

As used herein, HP indicates high pressure, MP indicates medium pressure, and LP indicates low pressure.

The article "Urea-melamine plant integration", Nitrogen+Syngas 321, January-February 2013, p.44-54, describes approaches to urea-melamine integration. One approach is condensing the melamine plant off-gas by mixing it with a lean carbamate solution received from the urea plant. Another approach, used in case of urea plants of the Snamprogetti type, is described as condensing the off-gas at 20 bar(g) inside the melamine plant itself and delivering the resulting carbamate solution to the urea high pressure section. Another approach for such a type of urea plants is described as condensing the off-gas in the low pressure, medium pressure, or high pressure section of the urea plant, as appropriate, in the existing condenser or in a condenser added in parallel.

Various melamine production processes are illustrated in Ullmann's Encyclopaedia of Industrial Chemistry, Chapter Melamine, 2003.

US 2016/0194293 describes an integrated process for urea and melamine production, wherein off-gas from the melamine plant is condensed at medium pressure (20-30 bar) in a condenser which also receives carbamate from the low pressure recovery section of the urea plant. In one embodiment, the off-gas from the melamine plant is condensed in a first medium pressure (MP) carbamate condenser also receiving carbamate solution from the low pressure (LP) recovery section. The effluent from the condenser is supplied to a second MP carbamate condenser also receiving a gas stream from a dissociator which receives a part of the urea synthesis solution directly from the reactor; another part of the urea synthesis solution is supplied to a high pressure $CO_2$ stripper. The urea plant uses a high pressure (HP) scrubber. Gas from the reactor is supplied to the scrubber, where it is scrubbed with carbamate solution, and non-condensed gas is vented as "inert gases". A part of the $CO_2$ feed is supplied to a LP carbamate condenser.

Another reference for the coupling of urea plants and melamine plants is US 2007/0282102.

A high pressure scrubber of a urea plant is a complex and costly piece of equipment with certain safety risks due to operation at high pressure and the concentration of inert gas. It is noted that inert gas often contains $O_2$ used for preventing corrosion by passivation in the synthesis section, often supplied as passivation air also containing $N_2$, as well as $H_2$ from the $CO_2$ feed. A need to avoid the formation of explosive $H_2/O_2$ mixtures in places in urea plants where non-condensable gases are vented, is discussed in Ullmann's Urea, p.25. Generally, it is desired to reduce the number of pieces of HP equipment. A background reference discussing the advantages of dispensing with an HP scrubber is US 2019/0015811.

US 2016/0318883 shows in FIG. 10 a process scheme of a urea plant with a $CO_2$ HP stripper, wherein the stripped urea solution is subjected to adiabatic flashing. The resulting gas is subjected to condensation together with off-gas from the reactor and off-gas from a melamine plant.

SUMMARY

The invention seeks to provide for better plants and processes for the integrated production of urea and melamine, for instance with relatively low specific steam consumption (energy consumption).

The invention generally pertains to a urea production process and plant with, in series, an MP first carbamate condenser for condensing at least a urea synthesis section off-gas to give a medium pressure (MP) condenser effluent, gas/liquid separation of the MP condenser effluent to give a gas stream and a liquid stream, and a second carbamate condenser receiving off-gas from melamine production and said liquid stream.

An aspect of the invention pertains to an integrated urea and melamine production process comprising: producing urea in a high pressure urea synthesis section of the stripping type, giving a urea solution also comprising carbamate, which urea solution is preferably stripped urea solution, and a separate urea synthesis section off-gas stream comprising inert gases, and $NH_3$ and $CO_2$; producing melamine thereby making available a melamine off-gas stream; preferably subjecting the urea solution, which urea solution is preferably stripped urea solution, to a MP treatment wherein at least some of the carbamate contained in the urea solution is dissociated into $CO_2$ and $NH_3$, giving MP urea solution and a first MP gas stream; subjecting at least a part of the urea synthesis section off-gas stream and preferably the first MP gas stream to condensation in a first MP carbamate condenser to give an MP condenser effluent and/or subjecting gas from an off-gas outlet of the urea synthesis section and preferably gas from the MP treatment to the condensation in the first MP carbamate condenser; subjecting the MP condenser effluent to gas/liquid separation to give a second MP gas stream comprising said inert gases, and a first MP carbamate solution; subjecting the melamine off-gas stream to condensation in a second MP carbamate condenser in the presence of at least a part of the first MP carbamate solution, to give a second MP carbamate solution; and supplying the second MP carbamate solution directly or indirectly to the urea synthesis section.

The invention also pertains to an integrated urea and melamine production plant comprising: a high pressure urea synthesis section of the stripping type, having an outlet for urea solution also comprising carbamate, and a separate outlet for a urea synthesis section off-gas stream comprising inerts, $NH_3$ and $CO_2$; a melamine production section having an outlet for a melamine off-gas stream; preferably an MP treatment unit for treating the urea solution at medium pressure, wherein at least some of the carbamate contained in the urea solution is dissociated into $CO_2$ and $NH_3$, having an outlet for MP urea solution and an outlet for a first MP gas stream; a first MP carbamate condenser for subjecting at least a part of the urea synthesis section off-gas stream and preferably the first MP gas stream to condensation to give an MP condenser effluent; a gas/liquid separator for subjecting the MP condenser effluent to gas/liquid separation to give a second MP gas stream and a first MP carbamate solution; a second MP carbamate condenser for subjecting the melamine off-gas stream to condensation in the presence of at least a part of the first MP carbamate solution, to give a second MP carbamate solution; and a liquid flow line for supplying the second MP carbamate solution directly or indirectly to the urea synthesis section.

The invention also pertains to a method of modifying an existing urea plant, the existing urea plant comprising: a high pressure urea synthesis section of the stripping type, having an outlet for urea solution also comprising carbamate and a separate outlet for a urea synthesis section off-gas stream comprising inerts, $NH_3$ and $CO_2$; wherein the method involves: adding, if not already present in the existing urea plant: a melamine production section having an outlet for a melamine off-gas stream; preferably an MP treatment unit for treating the urea solution at medium pressure, wherein at least some of the carbamate contained in the urea solution is dissociated into $CO_2$ and $NH_3$, having an outlet for MP urea solution and an outlet for a first MP gas stream; a first MP carbamate condenser for subjecting at least a part of the urea synthesis section off-gas stream and preferably the first MP gas stream to condensation to give an MP condenser effluent; wherein the method comprises adding: a gas/liquid separator for subjecting the MP condenser effluent to give gas/liquid separation give a second MP gas stream and a first MP carbamate solution; a second MP carbamate condenser for subjecting the melamine off-gas stream to condensation in the presence of at least a part of the first MP carbamate solution, to give a second MP carbamate solution; and a liquid flow line for supplying the second MP carbamate solution directly or indirectly to the urea synthesis section.

BRIEF DESCRIPTION OF THE DRAWINGS

Any embodiments illustrated in the figure are examples only and do not limit the invention.

DETAILED DESCRIPTION

The present disclosure is based, broadly, on the judicious insight that the condensation of the melamine off-gas is advantageously conducted with a relatively low water content of the resulting second carbamate solution, by virtue of the upstream gas/liquid separation. Thereby, advantageously the condensation of the melamine off-gas can be performed by exploiting the amount of water already contained in the first MP carbamate solution; the minimum amount of water in the first MP carbamate condenser being given by the need to sufficiently condense, as carbamate, the $NH_3$ and $CO_2$ from the urea synthesis section off-gas. The inert gas in the urea synthesis section off-gas, e.g. passivation air, does not negatively affect the melamine off-gas condensation temperature and pressure and does not negatively affect the water content of the carbamate recycle stream. The presence of non-condensable inert gas in the second MP carbamate condenser would result in a lower condensation temperature, for a given operating pressure of the second MP carbamate condenser.

The present invention concerns the coupling of a melamine plant with a urea plant by supplying the off-gas of the melamine plant, which comprises $CO_2$ and $NH_3$ to the urea plant, in particular indirectly to the high pressure synthesis section.

The inventive integrated urea and melamine production process comprises the production of urea and the production of melamine. Integrated, as used herein, means that melamine off-gas (i.e. off-gas from the melamine plant) is supplied, after condensation, to the high pressure urea synthesis section. The production of urea involves producing urea in a high pressure urea synthesis section of the stripping type, yielding a urea solution, comprising urea and water and also comprising carbamate, and yielding a separate urea synthesis section off-gas stream comprising inerts, $NH_3$ and $CO_2$. The inert gases are non-condensable for the purposes of the inventive process, and comprise e.g. $N_2$ and $O_2$. As an alternative or in addition to the term 'inerts', it can be specified that the off-gas contains gaseous components other than $NH_3$, $CO_2$ and $H_2O$.

The urea synthesis section off-gas stream as obtained from the urea synthesis section comprises, e.g. at least 2.0 vol. % inerts, or e.g. at least 4.0 vol. %, e.g. 2 to 12 vol. % inerts, based on total inerts, and/or wherein inerts are components other than $NH_3$, $CO_2$ and $H_2O$; and/or the off gas stream contains at least 2.0 vol. % of $N_2$, $O_2$ $H_2$ and $CH_4$ in total, e.g. at least 4.0 vol. %, e.g. in the range 2.0-10 vol. %; or 4.0-10%, or 4.0-8.0 vol. %.

The urea production involves the reaction of $NH_3$ and $CO_2$ to form carbamate and the dehydration of carbamate to urea and water. The high pressure urea synthesis section comprises a reaction zone operated at above 100 bar, preferably above 120 bar, and a high pressure stripper, operated at a pressure above 80 bar, for instance above 120 bar. The stripper is e.g. a $CO_2$ stripper or a thermal stripper. The synthesis section also comprises a condensation section for condensing gas from the stripper, operating at a pressure above 80 bar, or above 120 bar. The urea synthesis section off-gas stream originates typically from the reactor and/or from the carbamate condenser that are comprised in the synthesis section.

The process involves the production of melamine thereby making available a melamine off-gas stream. The melamine off-gas stream has a pressure of at least 10 bar and/or less than 130 bar, or less than 80 bar, or less than 60 bar, or less than 40 bar, e.g. 10-130 bar, or 10-80 bar, or 10-60 bar, or 10-40 bar. The melamine off-gas comprises $NH_3$ and $CO_2$. The melamine production uses urea as feedstock. The melamine synthesis pressure is typically above 70 bar, typically at least the gaseous component of the melamine synthesis effluent is depressurized to a pressure of less than 80 bar, more preferably less than 60 bar or less than 40 bar, and typically at least 10 bar or at least 20 bar.

The process preferably involves subjecting the urea solution from the synthesis section, preferably the stripped urea solution from the HP stripper, to a medium pressure treatment, i.e. a treatment at medium pressure, e.g. at a pressure of at least 10 bar and/or less than 80 bar. In this treatment at least some of the carbamate contained in the urea solution is dissociated into $CO_2$ and $NH_3$, thereby obtaining a first MP gas stream, and an MP urea solution.

The highly preferably used MP treatment generally involves depressurization of the urea solution from HP to MP, using a depressurization unit, e.g. a valve, thereby releasing gas from the solution, and gas/liquid separation of the first MP gas stream from the urea solution. The depressurization causes the spontaneous dissociation of carbamate contained in the urea solution into $NH_3$ and $CO_2$ which are at least in part released as gas from the solution, i.e. flashing, such that the first MP gas stream is formed. Hence, the MP treatment preferably involves flashing, which flashing optionally is combined with heating.

The treatment may, for example, involve adiabatic flashing. Adiabatic flashing involves depressurization and gas/liquid separation.

The MP treatment may also involve, e.g., depressurization to MP, heating at MP, and gas/liquid separation at MP. The treatment may also involve, e.g., depressurization to MP, gas/liquid separation (e.g. flashing) at MP, which flashing is e.g. adiabatic, heating of the urea solution at MP, and gas/liquid separation at MP, preferably with these three steps in this order. Heating at MP can be carried out using heat exchange with a heating fluid, such as e.g. steam, steam condensate, or process-process heat exchange with fluid in the synthesis section, for instance the MP heating is carried out inside the tube bundle of a pool condenser or pool reactor comprised in the urea synthesis section. Optionally, the MP urea solution after the gas/liquid separation is contacted with the gas from the MP (adiabatic) flash, to rectify the urea solution at MP, with the rectified urea solution expanded to LP and supplied to an LP dissociator of an LP recovery section, and with the gas from the MP rectification unit being supplied, together with urea synthesis section off-gas and also with preferably gas from said MP gas/liquid separation.

Optionally, the treated urea solution is further subjected, at medium pressure, to counter-current contact with $CO_2$, to remove $NH_3$ from the treated urea solution.

The process involves subjecting a part or all of the urea synthesis section off-gas stream, preferably with a part or all of the first MP gas stream, to condensation at medium pressure in a first MP carbamate condenser to give an MP condenser effluent. The effluent is in particular a fluid stream comprising gas and liquid at medium pressure.

The process furthermore involves subjecting the MP condenser effluent to gas/liquid separation, at medium pressure, to give a second MP gas stream and a first MP carbamate solution. The separation is for instance performed in a gas/liquid separation unit having a gas outlet and a liquid outlet. However, it is also possible that the separation is carried out inside the first MP carbamate condenser in embodiments wherein the first MP carbamate condenser has separate outlets for gas and liquid. It is also possible that the gas/liquid separation unit (separator) and the first MP carbamate condenser are integrated in a single vessel or apparatus, for instance with gas/liquid separation at an outlet side.

The process furthermore involves subjecting the melamine off-gas stream to condensation, at medium pressure, in a second MP carbamate condenser in the presence of at least a part (preferably at least 90 wt. %) of the first MP carbamate solution, to give a second MP carbamate solution. The second MP carbamate condenser is operated at a pressure in the MP range (e.g. 10 to 80 bar), or suitably at 10-130 bar. The pressure of the second MP carbamate condenser may be the same or different as the pressure of the first MP carbamate condenser, preferably is no more than 1 bar lower than the pressure in the first MP carbamate condenser. The process also involves supplying the second MP carbamate solution directly or indirectly to the urea high pressure synthesis section. The carbamate can then be converted into urea in the urea synthesis section.

The step of producing melamine is typically carried out in a melamine plant of the non-catalytic high pressure type (above 70 bar melamine synthesis pressure), i.e. in a non-catalytic high pressure melamine reactor. The melamine synthesis is based on the pyrolysis of molten urea, and $CO_2$ and $NH_3$ are formed as by-products of the melamine formation reaction.

The urea feedstock may originate from the same urea plant as receiving the melamine off-gas, or from a different urea plant, or from a combination thereof; in all these embodiments the production of urea and melamine is integrated by the processing of the melamine off-gas.

The melamine synthesis is conducted at a pressure above 70 bar, typically at a pressure less than 130 bar. An example suitable melamine production process operated at 80 bar is described in EP2385043A1. US 2004/0162429A1 illustrates another example suitable melamine production process with a washing section for the raw off-gas using urea melt to form anhydrous off-gas.

In some embodiments, the melamine synthesis pressure is more than 10 bar lower, e.g. more than 20 bar lower, than the urea synthesis pressure, and e.g. at least 10 bar lower or at least 20 bar lower than the pressure of the HP reactor, the HP stripper and the HP carbamate condenser. In some embodiments, the melamine synthesis pressure is between 70 and 90 bar and the urea synthesis pressure is at least 120 bar, e.g. 120-200 bar.

The step of making available of the melamine off-gas stream for instance involves washing a raw off-gas stream from a melamine synthesis reactor, preferably with urea. The raw off-gas stream can be obtained by subjecting the melamine synthesis mixture or the melamine synthesis effluent to gas/liquid separation to separate molten melamine from the gaseous phase, to give a raw off-gas stream containing minor amounts of melamine. The process typically involves washing of the raw off-gas stream to recover melamine, yielding a purified off-gas. The washing involves, e.g., water washing or urea washing; i.e. scrubbing the raw off-gas stream with water or with urea. In principle, any method for separating melamine from the off-gas can be used; anhydrous separations being preferred.

The process furthermore for example involves depressurizing the raw off-gas stream and/or depressurizing the purified off-gas. The purified off-gas is supplied, in the gaseous phase, to the second MP carbamate condenser in the inventive process.

The melamine off-gas stream, in particular after the washing, for example contains less than 15 wt. % water, or less than 10 wt. % water, or less than 2 wt. % water, water indicating $H_2O$, relative to the total gas stream; for example in embodiments with urea washing; or preferably less than 15 vol. % $H_2O$, or less than 10 vol. % or less than 2 vol. % $H_2O$. For example urea washing may yield anhydrous off-gas with less than 0.5 wt. % water. In embodiments with relatively low water content of the melamine off-gas, optimum use can be made of the water fraction of the first MP carbamate solution for the condensation of the melamine off-gas. The melamine off-gas comprises e.g. at least 95 vol. % or at least 98 vol. % $NH_3$ and $CO_2$ in total.

The melamine off-gas contains e.g. less than 0.10 vol. % inert gas, e.g. negligible inert gas.

The melamine off-gas is made available typically at a pressure in the range of 10 to 130 bar, e.g. 10 to 80 bar, preferably 15 to 45 bar, more preferably 20 to 30 bar. In some embodiments, the off-gas is made available at a pressure that is more than 10 bar lower, e.g. more than 20 bar lower, than the urea synthesis pressure, and e.g. at least 10 bar lower or at least bar lower than the pressure of the HP synthesis section, i.e. the pressure of each of the HP reactor, the HP stripper and the HP carbamate condenser.

In the inventive process, the melamine off-gas is condensed to form a second carbamate solution, using the water fraction of the first MP carbamate solution. Hence, second carbamate solution contains the water fraction of the first MP carbamate solution. Hence, at least a part of the first MP carbamate solution is present in the condensation zone, in particular the second MP carbamate condenser, which receives the melamine off-gas The resulting second carbamate solution has a certain minimum water content to prevent crystallization of carbamate at a given temperature and hence condensation pressure, for a given N/C ratio of the carbamate solution. The minimum water content decreases with increasing temperature and increasing condensation pressure. As the carbamate solution resulting from the condensation of the melamine off-gas is supplied to the urea synthesis section, in particular to the urea synthesis zone or urea synthesis reactor, the water content is desired to be low, since the presence of water in the urea synthesis zone or reactor is detrimental to the urea production.

In the present invention, very advantageously, the condensation of the melamine off-gas is conducted with a relatively low water content of the resulting second carbamate solution, by virtue of the upstream gas/liquid separation.

Thereby, advantageously the condensation of the melamine off-gas can be performed by exploiting the amount of water already contained in the first MP carbamate solution; the minimum amount of water in the first MP carbamate condenser being given by the need to sufficiently condense, as carbamate, the $NH_3$ and $CO_2$ from the urea synthesis section off-gas.

In the present invention, in a first aspect, the urea synthesis section off-gas is advantageously depressurized to medium pressure and subjected to condensation at medium pressure. Thereby, no high pressure scrubber needs to be used, which advantageously simplifies the HP urea synthesis section, in particular for urea plants of the $CO_2$ stripping type.

An aspect of the invention pertains to the use of two MP carbamate condensers in series, with the first MP carbamate condenser used for subjecting the urea synthesis section off-gas to condensation and the downstream second MP carbamate condenser used for condensing the melamine off-gas. The melamine off-gas condensation is improved by including a gas/liquid separation unit in the fluid flow line from the first to the second MP carbamate condenser. Thereby, the condensation temperature in the second MP carbamate condenser can be higher than in the first MP carbamate condenser, for instance also in embodiments wherein the absolute total pressure in the second MP carbamate condenser is lower than or substantially the same as in the first MP carbamate condenser. In any case the removal of the inert, non-condensable, gas from the effluent of the first MP carbamate condenser upstream of the second MP carbamate condenser allows to achieve a lower water content of the second carbamate solution at the liquid outlet of the second MP carbamate condenser than can be achieved without such gas/liquid separation. As the carbamate solution is recycled to the HP urea synthesis section, this improves urea conversion in the urea synthesis section. Optionally, the first carbamate solution is pumped to the second MP carbamate condenser.

Preferably the condensation temperature in the second MP carbamate condenser is at least 5° ° C. higher, than in the first MP carbamate condenser, e.g. at least 10° C. higher, such as 10° C. to 20° C. higher.

The first carbamate solution from the first MP carbamate condenser for example has a water content in the range of 22 to 26 wt. %.

The water content in the second MP carbamate condenser is preferably 1-5 wt. % lower than in the first MP carbamate condenser, as percentage points.

Preferably, the N/C ratio in the first MP carbamate condenser is in the range 2.0 to 2.5, more preferably in the range 2.1-2.4, such as e.g. about 2.3, based on liquid outlet composition. With these N/C values, advantageous sufficient complete condensation can be obtained with a relatively low amount of $NH_3$ in the second MP gas stream.

The first MP carbamate condenser may comprise one or more stages. Furthermore, optionally the urea synthesis section is subjected to condensation upstream of the first MP carbamate condenser, wherein gas from this upstream condensation is supplied to the first MP carbamate condenser. Optionally, the first MP gas stream is subjected to condensation upstream of the first MP carbamate condenser, wherein gas from this upstream condensation is supplied to the first MP carbamate condenser. Preferably, the plant comprises a condenser receiving both gas originating from a gas outlet of the HP urea synthesis section and gas from a gas outlet of the MP treatment unit; and the process involves a condensation step carried out in a condensation zone that receiving both gas originating from a gas outlet of the HP urea synthesis section and gas from a gas outlet of the MP treatment unit, i.e. receives at least a part, e.g. all, of the urea synthesis section off-gas and at least a part, e.g. all, of the first MP gas stream.

Preferably, the carbamate condensation in the first MP carbamate condenser is carried out in heat exchanging contact with urea solution to be heated, in particular with urea solution originating, directly or indirectly, from an LP dissociator, to give heated urea solution. This heating, preferably with water removal, is used e.g. to concentrate urea solution from about 72 wt. % urea to about 75-80 wt. % urea (urea including biuret). Preferably, the urea solution is at subatmospheric pressure, e.g. 0.3-1.0 bar. The plant for instance comprises a shell-and-tube heat exchanger with the condensation of the first MP gas stream and urea synthesis off-gas stream in the shell, i.e. with condensation of gas from the MP treatment and gas from the urea synthesis section in the shell, and heating of urea solution in the tubes; more preferably with vertical tubes. Shell, as used for shell-and-tube heat exchangers, refers to the shell-side space of the heat exchanger. Optionally, the urea solution is subjected to gas/liquid separation to remove the water vapour downstream of the tubes; this gas/liquid separation of the urea solution is separate and distinct from the gas/liquid separation of the condense effluent, i.e. the effluent from the shell. In an example embodiment, the shell has an outlet for effluent containing both liquid and gas, and the effluent from the shell is subjected to gas/liquid separation in a separate unit. In the embodiment with a shell around a vertical tube bundle, the gas inlet into the shell is preferably at the bottom of the shell and the outlet for biphasic effluent is at the top, or vice versa.

In other embodiments, the first MP carbamate condenser is for instance an absorber, i.e. not involving indirect heat exchange with a cooling liquid; for instance if the amount of urea synthesis section off-gas is small.

Optionally, the first MP carbamate condenser has a first outlet for liquid and a separate second outlet for gas, and the gas/liquid separation is performed inside the condenser; e.g. the outlets are vertically spaced, with a bottom liquid outlet and a top gas outlet.

Generally, the process involves gas/liquid separation of the carbamate solution formed in the first MP carbamate condenser from non-condensed gas in the first MP carbamate condenser, with selectively the carbamate solution being supplied to the second carbamate condenser. Preferably, the separated gas is expanded to LP, and supplied in part or entirely to a unit operating at LP, e.g. to a separate absorber or scrubber. The gas/liquid separation can be carried out inside the first MP carbamate condenser or in a separate unit.

The second MP carbamate condenser may comprise one or more stages. Preferably, the carbamate condensation in the second MP carbamate condenser is carried out in heat exchanging contact with urea solution to be heated, e.g. with urea solution originating, directly or indirectly, from an LP dissociator; more preferably with the heated urea solution from (the tube side of) the first MP carbamate condenser. Preferably, the urea solution is at subatmospheric pressure, e.g. 0.3-1.0 bar. The plant for instance comprises a shell-and-tube heat exchanger with the condensation of the melamine off-gas in the shell and with heating of urea solution in the tubes, preferably with further heating of said heated urea solution in the tubes. The pressure of the tubes is e.g. 0.2-0.5 bar. Optionally, the urea solution is further heated downstream of the heating in the second MP carbamate condenser, e.g. with steam. This further heating may be carried out e.g. in a single shell-and-tube heat exchanger having a shell (shell side space) divided in two compartments, a first compartment used as said second MP carbamate condenser and a second compartment with steam. The first shell compartment for instance has an inlet for gas at the bottom and an outlet for biphasic fluid effluent at the top, or vice versa, in particular with a vertical tube bundle. The urea solution stream is optionally subjected to gas/liquid separation to remove the water vapour downstream of the tubes. In a preferred embodiment, a vertical tube bundle is used with an inlet for the urea solution at the upper end of the tube bundle, with liquid flowing down in the tubes and gas flowing up in operation. A urea melt with at least 95 wt. % urea is for instance obtained from the tubes.

In other embodiments, the second MP carbamate condenser is for instance an absorber, i.e. not involving indirect heat exchange with a cooling liquid; for instance if the amount melamine off-gas is relatively small.

Preferably, the first and second MP carbamate condenser are both in heat exchanging contact, through a wall, with an evaporation stage for heating urea solution, e.g. as shell-and-tube heat exchanger with condensation in the shell and urea solution heating in the tubes. Preferably, the first MP carbamate condenser is in heat exchanging contact with a first evaporation stage, the second MP carbamate condenser is in heat exchanging contact with a second evaporation stage, and urea solution is supplied from the first evaporation stage, preferably through gas/liquid separation, to the second evaporation stage. Thereby, beneficially lower inert content in the second MP carbamate condenser contributes to further concentrating the urea solution in the second evaporation stage. The increased urea concentration by water evaporation contributes to providing a urea melt suitable e.g. for melamine production or for urea finishing.

Optionally, the second MP carbamate condenser has a first outlet for liquid and a separate second outlet for gas. Optionally, the second MP carbamate condenser has an outlet for effluent containing both gas and liquid, that is connected to a gas/liquid separation unit, wherein said gas/liquid separation unit has a liquid outlet that is in liquid flow connection with the reaction zone of the urea synthesis section. Gas from the second MP carbamate condenser is for instance sent to an absorber, operated e.g. at MP. Gas from the second MP carbamate condenser, if obtained as a separate stream, comprises e.g. at least 90 vol. % or at least 98 vol. % total $NH_3$ and $CO_2$.

If necessary, an aqueous stream, e.g., process condensate or cleaned process condensate, is supplied to the second MP carbamate condenser, in addition the first MP carbamate solution. Preferably, no additional water is supplied to the second MP carbamate condenser, additional to the first carbamate stream. Optionally, the process involves subjecting urea solution originating from the urea synthesis section to concentration by water evaporation to form a concentrated urea solution or melt having a concentration of at least 80 wt. % urea including biuret, and using a part of the concentrated urea solution or melt for purposes other than melamine production, e.g. for the production of solid or liquid fertilizer. The water vapor from the evaporation can be condensed and be supplied, typically in part, directly or indirectly, to the second MP carbamate condenser, e.g. through the first MP carbamate condenser.

The second MP gas stream, from the first MP carbamate condenser, is for example supplied to an MP scrubber which preferably also receives a carbamate stream from an LP recovery section of the urea plant, in particular from an LP carbamate condenser of the urea plant. The MP scrubber has a liquid outlet that is preferably connected to an inlet of the first MP carbamate condenser. The MP scrubber has a gas outlet which is connected, e.g., to an absorber, for instance an LP absorber. The inerts from the urea synthesis section are hence preferably supplied to said absorber, and can be vented from said absorber. Liquid from the absorber is typically supplied directly or indirectly to a wastewater treatment section. The absorber uses for instance a scrub liquid, such as a purified process condensate.

The second MP carbamate solution is supplied, directly or indirectly, to the HP urea synthesis section, by a liquid flow line. The carbamate solution is typically pumped to the HP urea synthesis section, typically after gas/liquid separation to remove any uncondensed vapour. The vapour is for example also supplied to the MP scrubber. The carbamate solution is for instance supplied directly to the reactor, or to the HP carbamate condenser.

The urea synthesis section is of the stripping type and comprises an HP stripper and a reaction zone and a condensation zone. The reaction zone and condensation zone are for example provided as zones in a single vessel, such as in the case of a horizontal pool reactor. A pool reactor can also be combined with a vertical urea reactor. The reaction zone and condensation zone can also be provided for example as separate units, such as a urea reactor, typically a vertical urea reactor, and an HP carbamate condenser. The HP synthesis section has a liquid outlet for stripped urea solution.

The urea reactor is typically a vertical urea reactor, with one or more inlets at the bottom and outlets for withdrawing urea solution from an upper part of the reactor, e.g. with a downcomer; and typically provided with trays. The reactor generally has an inlet for carbamate solution from the HP carbamate condenser.

The HP carbamate condenser is typically a shell-and-tube heat exchanger. A suitable HP carbamate condenser is e.g. a horizontal carbamate condenser with a U-shaped tube bundle, with cooling fluid in the tubes and with condensation taking place in the shell. Also possible is, for example, a vertical carbamate condenser with condensation in the shell and a U-shaped tube bundle with cooling fluid in the tubes, or e.g. a vertical shell-and-tube heat exchanger with condensation in the tubes, e.g. with gas to be condensed provided as bubbles in the tubes.

In another embodiment, the HP carbamate condenser is a shell-and-tube heat exchanger with condensation in the tubes, e.g. a kettle-type boiler or a falling film condenser.

Optionally, the reactor and condenser are combined in a single vessel, for instance as a pool reactor. A pool reactor is a horizontal vessel with a U-shaped tube bundle horizontally extending over a part of the vessel and with condensation in the shell side space at the tube bundle and with a reaction part in a part of the shell side space between the tube bundle and the shell (wall) of the vessel. The shell-side space of a pool reactor has an outlet for liquid connected to the reactor, and an inlet for gas from the stripper.

Generally, the cooling fluid of the HP carbamate condenser is for example, boiler feed water, or urea solution to be heated, or said cooling fluids are e.g. used in combination in two separate tube bundles.

The HP stripper is a heat exchanger configured for a falling film of urea solution in counter-current contact with a gas flow, having an inlet for urea solution at the top, an outlet for stripped urea solution at the bottom and an outlet for a gas stream at the top connected, for at least a part of that gas stream, to the HP carbamate condenser. The stripper is typically a shell-and-tube heat exchanger with heating fluid in the shell and urea solution in the tubes. The HP stripper is preferably a $CO_2$ HP stripper having an inlet for $CO_2$ used as strip gas at the bottom. The HP stripper may also be a thermal stripper.

The HP synthesis section may comprise further equipment pieces, such as an ejector or a carbamate separator, depending on the type of synthesis section used.

In a preferred embodiment, the stripper is a $CO_2$ HP stripper, using at least a part, or all, of the $CO_2$ feedstock as strip gas, and the synthesis zone is operated with an N/C ratio of 3.0 to 3.5, for instance 3.0-3.2, and/or e.g. with a synthesis pressure of 120-160 bar, e.g. (about) 140 bar; preferably these N/C ratio and pressures in combination.

With higher N/C ratio above 3.5 in the synthesis section, condensation of the urea synthesis off-gas into a carbamate solution at MP, especially 10-30 bar, becomes difficult or requires special measures.

Preferably, the plant does not comprise a dedicated $NH_3$ recycle flow line in this embodiment with $CO_2$ HP stripping. Accordingly, the first MP carbamate condenser is preferably operated with substantially complete condensation of $NH_3$ (and $CO_2$). Supplying the first MP gas stream from the MP treatment, preferably MP treatment with temperature decrease of the urea solution, more preferably from MP adiabatic flash, to the first MP carbamate condenser, may advantageously contribute to this.

Preferably, the urea solution is subjected to high pressure $CO_2$ stripping prior to the MP treatment; accordingly preferably the stripped urea solution from the $CO_2$ HP stripper is subjected to the MP treatment, preferably with a lower urea solution temperature at the outlet than at the inlet, more preferably to adiabatic flashing. In such an embodiment, the first gas stream will have a sufficiently low N/C ratio so as to provide for optimum carbamate condensation at MP in combination with the urea synthesis section off-gas. Additionally, the MP flash may contribute to lower steam consumption of the HP stripper.

In an embodiment, the urea production uses HP thermal stripping, and the plant or process is e.g. of the Snamprogetti type. In an example embodiment, the urea solution from the thermal HP stripper is subjected to MP dissociation (as MP treatment) in a MP decomposer, which is for instance a shell-and-tube heat exchanger, e.g. with the urea solution in the tubes. The first MP gas stream from the MP decomposer, together with the urea synthesis section off-gas, is condensed in the first MP carbamate condenser. Effluent from the condenser is subjected to gas/liquid separation in an ammonia-carbamate separation column; the resulting second MP gas stream is for instance supplied to an ammonia condenser and the resulting first MP carbamate solution to the second MP carbamate condenser which also receives the melamine off-gas. The second MP carbamate solution from the second MP carbamate condenser is supplied to the synthesis section. The effluent from the ammonia condenser is subjected to gas-liquid separation and the resulting gas stream, containing inerts, is typically ultimately vented after further purification e.g. in an ammonia scrubber. Uncondensed gas from the second MP carbamate condenser is supplied, e.g., to an LP recovery section of the plant, or to a unit of the MP section, e.g. supplied directly or indirectly to the ammonia scrubber, or is vented.

In a further embodiment, the urea synthesis section comprises a $CO_2$ stripper and is e.g. of the ACES 21 type, as offered by Toyo. In an example embodiment of the process, the reactor is operated at a pressure of at least 150 bar and with an N/C ratio of above 3.5; and the HP striping uses $CO_2$ as strip gas. The stripped urea solution is supplied to the MP treatment in an MP decomposer, which is e.g. a shell-and-tube heat exchanger using steam for heating. The resulting first MP gas stream is supplied, directly or indirectly, to an MP absorber which is a heat exchanger, used for cooling, which also receives carbamate solution from an LP recovery section and which provides for gas/liquid separation. The first carbamate solution from the MP absorber is supplied to the second MP carbamate condenser also receiving the melamine off-gas. The effluent from the second MP carbamate condenser is subjected to gas/liquid separation; the liquid is supplied to the HP synthesis section, in particular to the HP carbamate condenser, through a HP carbamate pump. The HP carbamate condenser is e.g. a condenser with condensation in the shell and cooling fluid in a vertical U-shaped tube bundle.

In a further embodiment, the process involves HP $CO_2$ stripping and subjecting the stripped urea solution to the MP treatment by heating at MP, which heating at MP is carried out by flowing the liquid at MP through a tube bundle of an HP carbamate condensation unit operated with condensation of gas from the stripper in the shell at HP, e.g. by suppling the liquid at MP to a tube bundle of a pool reactor. The effluent from the tube bundle is subjected to gas/liquid separation to give the first MP gas stream. The process furthermore involves condensing said gas stream and the urea synthesis section off-gas in the first MP carbamate condenser; subjecting the resulting effluent to gas/liquid separation, and supplying the resulting first MP carbamate solution to the second MP carbamate condenser also receiving the melamine off-gas. A pool reactor is a horizontal vessel comprising a condensation zone and a reaction zone wherein the U-shaped tube bundle(s) are located in the condensation zone. The reaction zone is for instance provided between the bend of the U-shaped tube bundles and the shell.

In an embodiment, the urea synthesis section comprises a $CO_2$ HP stripper, and the process involves supplying a first part of the urea synthesis solution from the HP reaction zone to an MP dissociator, bypassing the HP stripper, and supplying a second part of the urea synthesis solution from the reactor to the HP stripper. The first part of the urea solution is expanded to MP pressure and subjected to the MP treatment, e.g. with adiabatic flashing, heating, and/or counter-current contact with an MP $CO_2$ gas stream; to give the first MP gas stream and the MP urea solution. The gas stream is condensed in the first MP carbamate condenser, together with off-gas from the urea synthesis section, to form the MP carbamate solution which is supplied, with MP gas/liquid separation, to the second MP carbamate condenser also receiving melamine off-gas. The gas from the MP gas/liquid separation contains inerts. The urea synthesis section typically contains no HP scrubber. Urea solution from the HP stripper and the MP urea solution are supplied to one or more LP recovery sections. The MP urea solution may be subjected to counter-current contact with MP $CO_2$ stream, the resulting MP gas stream may be supplied to the first and/or second MP carbamate condenser.

The MP urea solution from the MP treatment is typically expanded to LP and subjected to LP carbamate decomposition, typically by heating, to give a LP urea solution and an LP gas stream. The LP urea solution is typically supplied directly or indirectly to an evaporation section which typically comprises one or more vacuum evaporation stages to give a urea melt, with e.g. at least 95 wt. % urea including biuret, or at least 98 wt. % urea including biuret. The urea melt is, e.g., supplied in part or entirely to the melamine production section. In some embodiments, the urea melt is not supplied to the melamine production section and the melamine production section uses urea from another urea plant. In some embodiments, at least a part of the urea melt is subjected to finishing, i.e. solidification to form a solid urea product, such as granulation or prilling.

The vapor from the evaporation section is typically condensed and the resulting condensate is typically supplied to a wastewater treatment section, comprising e.g. a desorber and a hydrolysis unit, which section gives cleaned process condensate and a dilute carbamate solution.

In a preferred embodiment, 5 to 40 wt. % of the total urea produced in the high pressure urea synthesis section is supplied to the melamine synthesis zone or reactor, while remaining urea is sent to unit other than the melamine plant, e.g. a finishing section, or a unit for the production of liquid fertilizer. Preferably, the melamine production is exclusively fed with said part of 5 to 40 wt. % of the total urea produced. Suitably, the remaining urea part is subjected to concentration by water evaporation.

Preferably, the amount of the melamine off-gas stream corresponds to the conversion into melamine of an amount of urea of 5 to 40 wt. % of the total urea produced in the high pressure urea synthesis section. Larger amounts of melamine off-gas relative to urea production of the synthesis section may be in particular less advantageous for urea synthesis sections of the $CO_2$ stripping type as the amount of carbamate recycle becomes relatively large compared to the amount of feed $CO_2$.

The water vapour from the evaporation section is condensed to form process condensate, which is typically purified in a waste water treatment section using e.g. desorption and hydrolysis.

The LP gas stream is supplied to an LP carbamate condenser to give an LP carbamate solution. The LP carbamate solution is typically supplied directly or indirectly to the first MP carbamate condenser, for instance through an MP scrubber or MP absorber.

The LP carbamate condenser typically receives an aqueous stream to provide water to prevent precipitation of carbamate. The aqueous stream originates e.g. from the wastewater treatment section. The amount of water in the LP carbamate condenser can be set as appropriate, also for the water required in the first and second MP carbamate condenser.

Figure 1:
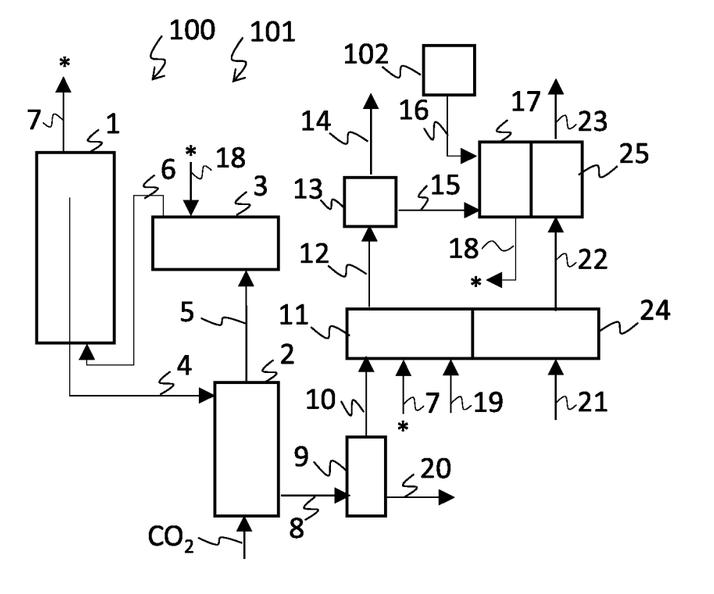
FIG. 1 schematically illustrates an example process scheme according to the invention.

FIG. 1 schematically illustrates an example urea production process scheme according to a non-limiting embodiment of the invention. It is noted that only some but not all of the units and connections shown in the figure are recited in the independent claims; the other units and connections are not mandatory and are preferably used. The urea plant (100) comprises an HP synthesis section (101) comprising a reactor (1), an HP stripper (2) and an HP carbamate condenser (3).

The urea reactor (1) is typically a vertical urea reactor with one or more inlets at the bottom and an outlet for urea synthesis solution (4) for withdrawing urea synthesis solution from an upper part of the reactor, optionally with a downcomer for urea synthesis solution. The reactor is for instance provided with trays.

The HP stripper (2) is illustrated as a $CO_2$ HP stripper receiving a part or all of the $CO_2$ feed. The stripper has an inlet for urea synthesis solution (4), an outlet for a gas stream (5) at the top to the HP carbamate condenser (3); and an outlet for a stripped urea solution (8) at a bottom part. In operation, the urea synthesis solution stream (4) or a part thereof is subjected to stripping in the HP stripper (2) to give the stripped urea solution (8). Optionally, a part of urea synthesis solution stream (4) may be provided directly to a unit for MP treatment (9), bypassing the HP stripper (2).

The HP carbamate condenser (3) is for example, a horizontal carbamate condenser with a U-shaped tube bundle, with a cooling fluid in the tubes and with condensation taking place in the shell. The HP carbamate stream (6) from the HP carbamate condenser (3) is supplied to the urea reactor (1).

The HP synthesis section (101) also has an inlet for $NH_3$ feed (not shown), e.g. to the HP carbamate condenser (3).

The HP synthesis section (101) has a separate outlet for a urea synthesis section off-gas stream (7). The outlet is for instance provided at the urea reactor (1) (as illustrated) or at the HP carbamate condenser (3). The urea synthesis section off-gas stream (7) comprises inerts, such as, e.g., one or more of: $O_2$ used for passivation, $H_2$ from the $CO_2$ feed, $CH_4$ and possibly other hydrocarbon comprised in the $CO_2$ feed, and argon and $N_2$ from the $CO_2$ and/or $NH_3$ feed, and as comprised in any air used for passivation. Passivation refers to corrosion prevention in the urea synthesis section. In embodiments, the urea synthesis section operates with e.g. at least 0.2 vol. % or at least 0.5 vol. % $O_2$ relative to the $CO_2$ feed; with any associated $N_2$ in embodiments wherein the $O_2$ is introduced as air into urea synthesis section. The passivation oxygen or air is e.g. added to the $CO_2$ feed.

It is noted that these gaseous components are generally non-condensable in a urea plant and are vented.

The stripped urea solution (8) is expanded from HP to MP and supplied to the unit for MP treatment (9), where at least gas/liquid separation takes place. The unit for MP treatment (9) is e.g. an adiabatic flash unit, or is e.g. a dissociator comprising a heating unit, such as a heat exchanger, with gas/liquid separation. The unit for MP treatment (9) has an outlet for a first MP gas stream (10) connected to a first MP carbamate condenser (11) and an outlet for an MP urea solution (20). The MP urea solution is supplied to an LP recovery section (not shown).

The first MP carbamate condenser (11) has an outlet for an MP condenser effluent (12) which comprises carbamate solution and gas.

The first MP carbamate condenser (11) is typically provided as a part of a heat exchanger and has a heat exchanging wall which is exposed on a first side to the condensing process medium of the first MP carbamate condenser and on a second side to a cooling fluid, such as urea solution.

The first MP carbamate condenser (11) is preferably provided as a shell-and-tube heat exchanger with cooling fluid in the tubes and with condensation in the shell. Preferably, in operation at least a part of the urea synthesis section off-gas stream (7) and the first MP gas stream (10) are subjected to condensation in a shell space of the first MP carbamate condenser (11) to give the MP condenser effluent (12), while a urea solution (21) is heated in tubes of the first MP carbamate condenser (11) to give a heated urea solution (22).

The first MP carbamate condenser (11) also receives the synthesis section off-gas stream (7) which includes inert components, $NH_3$ and $CO_2$.

The N/C ratio in the first MP carbamate condenser (11) is preferably in the range 2.0 to 2.5, more preferably in the range 2.1-2.4, such as e.g. about 2.3, based on liquid outlet. An preferred N/C ratio of max. 2.4 avoids loss of gaseous $NH_3$ through the second MP gas stream (14) and avoids the need for separate $NH_3$ condensation and liquid $NH_3$ recycle to the HP synthesis section.

Very advantageously, the combined condensation of the synthesis section off-gas stream (7) with the first MP gas stream (10) may provide for a molar ratio $NH_3$ to $CO_2$ in these ranges. In particular, the synthesis section off-gas stream (7) may have a relatively high $NH_3$ to $CO_2$ molar ratio, such as 3.0-4.0 and the first MP gas stream (10) may have a relatively low $NH_3$ to $CO_2$ molar ratio, such as less than 2.0, e.g. in the range 1.0-2.0. In particular with adiabatic flash of the stripped urea solution (8) in the MP treatment unit (9), the first MP gas stream (10) may have an $NH_3$ to $CO_2$ molar ratio of 1.0-1.5. The stripped urea solution (8) from a $CO_2$ HP stripper typically has a relatively low N/C ratio because of the upstream $CO_2$ stripping.

The MP condenser effluent (12) is subjected to gas/liquid separation (13), for example in a gas/liquid separation zone, at medium pressure to give a second MP gas stream (14) and a first MP carbamate solution (15) (a first MP carbamate liquid stream). Generally, the inert components of the urea synthesis feed streams end up in the second MP gas stream (14). The gas/liquid separation (or separation zone) is, e.g., a dedicated unit (as illustrated) or is e.g. integrated in a single unit with the first MP carbamate condenser. For example, the first MP carbamate condenser has two separate outlets, e.g. a top outlet for gas and a bottom outlet for liquid.

The relatively low N/C ratio in the first MP carbamate condenser (11) enables more complete condensation in that condenser (11) and a relatively low $NH_3$ content of the second MP gas stream (14). Thereby, in embodiments wherein the second MP gas stream (14) is supplied directly or indirectly to a scrubber or an absorber (not shown), e.g. an LP absorber, which e.g. has a liquid outlet connected to a waste water treatment section (WWT section). The increase of the load of the WWT is advantageously relatively small which contributes to better energy efficiency of the plant.

The first MP carbamate solution (15) is accordingly substantially degassed and is supplied in part or entirely, with a very low content of gaseous inert components, to a second MP carbamate condenser (17) which also receives an MP melamine off-gas stream (16) from a melamine production section (102).

The MP melamine off-gas stream (16) is at least in part, preferably essentially completely condensed and/or absorbed in the second MP carbamate condenser (17) to give a second MP carbamate solution (18) which is supplied, directly or indirectly, to the HP synthesis section (101), preferably to the HP carbamate condenser (3). Preferably, the second MP carbamate condenser (17) is for example provided as a shell-and-tube heat exchanger with condensation in the shell and with the tubes used as second evaporation stage (25). Preferably, in operation at least a part of the melamine off-gas stream (16) is subjected to condensation in the shell side space of the second MP carbamate condenser (17) to give the second MP carbamate solution (18), wherein the heated urea solution (22) is heated in tubes of the second MP carbamate condenser (17) to give the further heated urea solution (23).

The very low content of inert gas in the first MP carbamate solution (15), i.e. as obtained from the gas/liquid separation, permits operating the second MP carbamate condenser (17) at a relatively high temperature for any fixed absolute (or total) operating pressure of the second MP carbamate condenser (17), compared to processes wherein no gas/liquid separation is used, due to the lower partial pressure of inerts in the second MP carbamate condenser (17), and the corresponding higher partial vapour pressure of $NH_3$ and $CO_2$. The relatively high condensation temperature permits a lower water content of the second MP carbamate solution (18) without risk of crystallization or precipitation of carbamate, thereby reducing the water content of the reaction mixture in the reactor and advantageously increasing urea yield, i.e. increases the conversion into urea in the synthesis section. The water content of the first MP carbamate solution (15) is typically sufficient for operating the second MP carbamate condenser (17) and is typically set at the minimum necessary for safely operating the first MP carbamate condenser (11). The water content of the first MP carbamate solution (15) can by adjusted e.g. through the amount of aqueous liquid supplied to the LP carbamate condenser. Suitable sources of the aqueous liquid are dilute carbamate solutions from a wastewater treatment section, associated with an evaporation section, and cleaned process condensate from the wastewater treatment section.

The first MP carbamate condenser (11) also receives a carbamate solution stream (19) preferably originating directly or indirectly from an LP carbamate condenser (not shown). This carbamate solution stream (19) contains $H_2O$ that is used to prevent carbamate crystallization in the first and second MP carbamate condenser.

The first MP carbamate condenser (11) is in heat exchanging contact, through a wall, with the urea solution (21) to be heated in a first evaporation stage (24). The urea solution (21) originates, e.g., directly or indirectly from an LP recovery section (not shown). The heating gives the heated urea solution (22), which is supplied, after gas/liquid separation to remove water vapour, to the second evaporation stage (25) which is in heat exchanging contact, through a wall, with the second MP carbamate condenser (17), where the urea solution is heated to provide a further heated urea solution (23). This urea solution may in turn be heated further, e.g. by heat exchange using steam, to give a urea melt.

The invention also provides an integrated urea and melamine production plant preferably suitable for carrying out the inventive process. The plant comprises a gas/liquid separator or separation zone for subjecting the MP condenser effluent to gas/liquid separation; this separator or separation zone is e.g. integrated at a downstream side of the first MP carbamate condenser, or is e.g. provided as a separate unit. The gas/liquid separator or separation zone has a liquid outlet in liquid flow connection with an inlet of the second MP carbamate condenser. The gas/liquid separator or separation zone also has a separate gas outlet with a fluid connection to an inlet of preferably an absorber or scrubber, this absorber and scrubber preferably operate at LP.

Preferably, the melamine production section is of the non-catalytic, high pressure type.

Preferably the melamine production section comprises a melamine synthesis reactor and a washing section for washing a raw off-gas stream from the melamine synthesis reactor with urea.

Preferably the high pressure urea synthesis section is of the $CO_2$ stripping type comprising a high pressure $CO_2$ stripper having an outlet for urea solution connected to the MP treatment unit.

Preferably, the first MP carbamate condenser is in heat exchanging contact with a first evaporation stage, the second MP carbamate condenser is in heat exchanging contact with a second evaporation stage, and the plant comprises a liquid flow line for supplying urea solution from the first evaporation stage, preferably through gas/liquid separation, to the second evaporation stage. The first and second evaporation stage are also comprised in the plant; the first evaporation stage is connected to directly or indirectly receive urea solution originating from, in particular, the MP treatment unit, typically through an LP recovery section.

Also provided is a method of modifying an existing urea plant. The existing urea plant comprises an HP urea synthesis section of the stripping type, having an outlet for a urea solution also comprising carbamate, and a separate outlet for a urea synthesis section off-gas stream comprising inerts, $NH_3$ and $CO_2$. The method involves adding, if not already present, in the existing urea plant a melamine production section having an outlet for a melamine off-gas stream. Hence, in one embodiment, the existing plant is already for the integrated production of melamine and urea; in other embodiments the plant is modified into such a plant.

The method involves adding, if not already present, in the existing urea plant an MP treatment unit for treating the urea solution at medium pressure, wherein at least some of the carbamate contained in the urea solution is dissociated into $CO_2$ and $NH_3$, having an outlet for MP urea solution and an outlet for a first MP gas stream; and a first MP carbamate condenser for subjecting at least a part of the urea synthesis section off-gas stream and the first MP gas stream to condensation to give an MP condenser effluent. The method comprises adding a gas/liquid separator for subjecting the MP condenser effluent to gas/liquid separation to give a second MP gas stream and a first MP carbamate solution; a second MP carbamate condenser for subjecting the melamine off-gas stream to condensation in the presence of at least a part of the first MP carbamate solution, to give a second MP carbamate solution; and a liquid flow line for supplying the second MP carbamate solution directly or indirectly to the urea synthesis section. The modified plant is preferably a plant according to the invention and is preferably suitable for the inventive urea production process.

The term 'carbamate', as used herein, refers to ammonium carbamate, as that term is used in the field of urea production.

As used herein, for process streams of the urea plant (i.e. not for steam lines), high pressure (HP) is above 100 bar, for instance 120 to 300 bar, for example 140 to 200 bar. Medium pressure (MP) is for example 10 to 80 bar (including intermediate pressure of 30 to 70 bar), in particular 15 to 30 bar, and low pressure (LP) is for example 0 to 10 bar, in particular 1 to 8 bar or 2 to 5 bar. All pressures are bar absolute (bara).

The term 'typical' and 'in particular' are used to indicate features that can be used in some embodiments but that are not mandatory. Also preferred features are not mandatory.

For all instances of the phrase "at least a part" of a stream, preferably at least 50 wt. % or at least 90% of the stream is used, optionally the entire stream.

The N/C ratio for gas streams indicates the molar ratio of $NH_3$ to $CO_2$. The N/C ratio as used herein for the urea synthesis section reflects the composition of the so-called initial mixture before urea production, consisting only of $NH_3$, $CO_2$ and $H_2O$, as used in the art of urea plants, and is the molar ratio. The N/C ratio of a carbamate solution indicates the molar ratio of the corresponding amounts of $NH_3$ to $CO_2$, i.e. with the amounts of $NH_3$ respectively $CO_2$ taken on the basis of the total of the free and carbamate, with 1 mol carbamate corresponding to 2 mol $NH_3$ and 1 mol $CO_2$. The N/C ratio for carbamate condenser refers to the N/C ratio of the carbamate solution at the relevant outlet.

The term 'melamine off-gas' as used herein indicates an off-gas stream from the melamine production section and refers to a gas stream mainly containing $NH_3$, and $CO_2$, and possibly $H_2O$ and minor amounts inert gas.

The term 'first' as used herein for a unit or a step permits the presence of further, upstream, instances of such unit or step.

All preferences and details discussed in connection with the process, apply also for the plant, and vice versa. All preferences and details described in connection with the plant, apply also for the method of modifying a plant.

Embodiments of the invention will now be further illustrated by the following example(s) which do not limit the invention or the claims.

EXAMPLE 1

In a design example, an integrated urea melamine plant according to the process scheme of FIG. 1 with a capacity of 3700 MTPD (metric ton per day) urea, was designed to be operated with the process design parameters given in Table 1. 1200 MTPD urea was used for melamine production and the remaining urea was obtained as a solid urea product after finishing.

As illustrated in FIG. 1, the first MP carbamate condenser received urea synthesis off-gas and gas from MP treatment, and selectively the liquid from the first MP carbamate condenser was supplied to the second MP carbamate condenser which received melamine off-gas. Non-condensed gas from the first MP carbamate condenser was reduced to LP and processed separately.

The urea plant of the example comprised a HP $CO_2$ stripper and the MP treatment was adiabatic flash.

About 20-25 kg steam/ton urea could be saved by using two MP carbamate condensers in series with removal of inerts in between, compared to a reference process using a single MP carbamate condenser that receives urea synthesis section off-gas, melamine off-gas, gas from the MP treatment, and carbamate solution from a LP carbamate condenser. The steam consumption refers to the steam consumption of the HP stripper, and in particular to 20-25 bar steam used in the HP stripper. The lower water recycle to the urea synthesis permits operating the HP stripper with less heating and therefore lower steam consumption.

In Table 1, the percentage inerts refers to vol. % inert gas in the gas phase from the condenser (based on outlet temperature). Besides the inert gas, the gas phase comprises $NH_3$, $CO_2$ and $H_2O$.

Both MP carbamate condensers operate with the same (total) pressure of 24 bara, but the partial vapor pressure of $NH_3$ and $CO_2$ is higher in the second carbamate condenser than in the first, due to the lower level of inerts in the second carbamate condenser, such that the condensation temperature in the second carbamate condenser is higher. The higher temperature in turn permits operating the second carbamate condenser with a lower wt. % of the liquid phase without a risk of carbamate crystallization. Therefore, the amount of water (kg water per ton urea production) recycled from the second carbamate condenser to the urea synthesis section is lower than in a comparative embodiment wherein a single MP carbamate condenser is used that receives melamine off-gas, urea synthesis section off-gas, and gas from the MP treatment.

Both MP carbamate condensers are provided as the shell side compartment of a respective shell-and-tube heat exchanger, with gas to be condensed in the shell and urea solution, which is heated, in the tubes.

TABLE 1

| (shell side) | 1$^{st}$ MP carbamate condenser | 2$^{nd}$ MP carbamate condenser |
|---|---|---|
| Temperature (° C.) | 105-110 | 115-120 |
| Pressure (bara) | 24 | 24 |
| Water content (wt. %) | 24.5 | 20.1 |
| N/C ratio (liquid at outlet) | 2.3 | 2.35 |
| Inerts (vol. %) | ~40 | <0.05 |

The invention claimed is:

1. An integrated urea and melamine production process comprising:
    producing urea in a high pressure (HP) urea synthesis section of the stripping type, giving a stripped urea solution also comprising carbamate, and a separate urea synthesis section off-gas stream comprising inert gases, $NH_3$ and $CO_2$;
    producing melamine thereby making available a melamine off-gas stream;
    subjecting the stripped urea solution to medium pressure (MP) treatment wherein at least some of the carbamate contained in the stripped urea solution is dissociated into $CO_2$ and $NH_3$, giving an MP urea solution and a first MP gas stream;
    subjecting at least a part of the urea synthesis section off-gas stream and the first MP gas stream to condensation in a first medium pressure (MP) carbamate condenser to give an MP condenser effluent;
    subjecting the MP condenser effluent to gas/liquid separation to give a second MP gas stream comprising said inert gases, and a first MP carbamate solution;
    subjecting the melamine off-gas stream to condensation in a second MP carbamate condenser in the presence of at least a part of the first MP carbamate solution, to give a second MP carbamate solution; and
    supplying the second MP carbamate solution directly or indirectly to the urea synthesis section.

2. The process according to claim 1, wherein the melamine production is carried out in a non-catalytic high pressure melamine reactor.

3. The process according to claim 1, wherein the condensation temperature in the second MP carbamate condenser is at least 5° C. higher than in the first MP carbamate condenser.

4. The process according to claim 1, wherein the melamine off-gas stream contains less than 15 wt. % water.

5. The process according to claim 4, wherein the melamine off-gas stream contains less than 2 wt. % water.

6. The process according to claim 1, wherein the production of melamine involves washing a raw off-gas stream from a melamine synthesis reactor with urea.

7. The process according to claim 1, wherein the HP urea synthesis section is of the $CO_2$ stripping type and a urea synthesis solution from a reaction zone is subjected to high pressure $CO_2$ stripping prior to the MP treatment.

8. The process according to claim 7, wherein the MP treatment involves depressurization of the urea solution from HP to MP in a depressurization unit, thereby releasing gas from the solution, and gas/liquid separation of the first MP gas stream from the urea solution.

9. The process according to claim 1, wherein the first and the second MP carbamate condenser are both in heat exchanging contact with an evaporation stage for heating urea solution.

10. The process according to claim 9, wherein the first MP carbamate condenser is in heat exchanging contact with a first evaporation stage, the second MP carbamate condenser is in heat exchanging contact with a second evaporation stage, and a heated urea solution is supplied from the first evaporation stage.

11. The process according to claim 10, wherein the first MP carbamate condenser is provided as a shell-and-tube heat exchanger, wherein at least a part of the urea synthesis section off-gas stream and the first MP gas stream are subjected to condensation in a shell space of the first MP carbamate condenser to give the MP condenser effluent, wherein a urea solution is heated in tubes of the first MP carbamate condenser to give the heated urea solution, wherein the second MP carbamate condenser is provided as a shell-and-tube heat exchanger, wherein at least a part of the melamine off-gas stream is subjected to condensation in the shell side space of the second MP carbamate condenser to give the second MP carbamate solution, and wherein the heated urea solution is heated in tubes of the second MP carbamate condenser to give a further heated urea solution.

12. An integrated urea and melamine production plant comprising:
    a high pressure (HP) urea synthesis section of the stripping type, having an outlet for a stripped urea solution also comprising carbamate, and a separate outlet for a urea synthesis section off-gas stream comprising inerts, $NH_3$ and $CO_2$;
    a melamine production section having an outlet for a melamine off-gas stream;

an MP treatment unit for treating the urea solution at medium pressure, wherein at least some of the carbamate contained in the stripped urea solution is dissociated into $CO_2$ and $NH_3$, having an outlet for an MP urea solution and an outlet for a first MP gas stream;

a first MP carbamate condenser for subjecting at least a part of the urea synthesis section off-gas stream and the first MP gas stream to condensation to give an MP condenser effluent;

a gas/liquid separation zone for subjecting the MP condenser effluent to gas/liquid separation to give a second MP gas stream and a separate first MP carbamate solution;

a second MP carbamate condenser for subjecting the melamine off-gas stream to condensation in the presence of at least a part of the first MP carbamate solution, to give a second MP carbamate solution; and a liquid flow line for supplying the second MP carbamate solution directly or indirectly to the urea synthesis section.

13. The integrated urea and melamine production plant according to claim 12, wherein the melamine production section is of the non-catalytic, high pressure type, and comprise a melamine synthesis reactor and a washing section for washing a raw off-gas stream from the melamine synthesis reactor with urea, and wherein the HP urea synthesis section is of the $CO_2$ stripping type comprising a high pressure $CO_2$ stripper having an outlet for urea solution connected to the MP treatment unit.

14. The integrated urea and melamine production plant according to claim 12, wherein the first MP carbamate condenser is in heat exchanging contact with a first evaporation stage, the second MP carbamate condenser is in heat exchanging contact with a second evaporation stage, and the plant comprises a liquid flow line for supplying a heated urea solution from the first evaporation stage to the second evaporation stage.

15. A method of modifying an existing urea plant, the existing urea plant comprising:

a high pressure (HP) urea synthesis section of the stripping type, having an outlet for a stripped urea solution also comprising carbamate, and a separate outlet for a urea synthesis section off-gas stream comprising inerts, $NH_3$ and $CO_2$;

wherein the method involves:

adding, if not already present in the existing urea plant:

a melamine production section having an outlet for a melamine off-gas stream;

an MP treatment unit for treating the urea solution at medium pressure, wherein at least some of the carbamate contained in the urea solution is dissociated into $CO_2$ and $NH_3$, having an outlet for an MP urea solution and an outlet for a first MP gas stream;

a first MP carbamate condenser for subjecting at least a part of the urea synthesis section off-gas stream and the first MP gas stream to condensation to give an MP condenser effluent;

a gas/liquid separation zone for subjecting the MP condenser effluent to gas/liquid separation to give a second MP gas stream and a first MP carbamate solution;

and wherein the method comprises adding:

a second MP carbamate condenser for subjecting the melamine off-gas stream to condensation in the presence of at least a part of the first MP carbamate solution, to give a second MP carbamate solution; and a liquid flow line for supplying the second MP carbamate solution directly or indirectly to the urea synthesis section.

16. The process according to claim 8, wherein the depressurization unit is a valve.

17. The process according to claim 8, wherein the MP treatment is adiabatic flashing.

18. The process according to claim 10, wherein the heated urea solution is supplied from the first evaporation stage through a gas/liquid separation to the second evaporation stage.

19. The integrated urea and melamine production plant according to claim 14, wherein the liquid flow line for supplying a heated urea solution from the first evaporation stage to the second evaporation stage comprises a gas/liquid separator.

* * * * *